United States Patent [19]

Greenblatt et al.

[11] Patent Number: 5,672,258

[45] Date of Patent: *Sep. 30, 1997

[54] IMPEDANCE TYPE HUMIDITY SENSOR WITH PROTON-CONDUCTING ELECTROLYTE

[75] Inventors: Martha Greenblatt, Highland Park, N.J.; Shouhaa Feng, Changchun, China; Kandalam Ramanujachary, Maple Shade, N.J.; Pavel Shuk, Minsk, Belarus

[73] Assignee: Rutgers, The State University of New Jersey, New Brunswick, N.J.

[*] Notice: The term of this patent shall not extend beyond the expiration date of Pat. No. 5,393,404.

[21] Appl. No.: 395,412

[22] Filed: Feb. 27, 1995

Related U.S. Application Data

[63] Continuation-in-part of Ser. No. 79,237, Jun. 17, 1993, Pat. No. 5,393,404.

[51] Int. Cl.$^6$ .......................... G01N 27/26; G01N 27/406
[52] U.S. Cl. .......................... 204/430; 204/421; 204/424; 204/427; 205/788; 422/98
[58] Field of Search .......................... 204/153.22, 421, 204/424–429, 430; 422/98; 429/30–33, 191, 193; 205/788

[56] References Cited

U.S. PATENT DOCUMENTS

| | | |
|---|---|---|
| 3,276,910 | 10/1966 | Grasselli .......................... 136/86 |
| 3,776,831 | 12/1973 | Roy et al. .......................... 204/195 |
| 4,024,036 | 5/1977 | Nakamura et al. .......................... 204/129 |
| 4,321,577 | 3/1982 | Carlson .......................... 422/98 |
| 4,497,701 | 2/1985 | Murata et al. .......................... 204/430 |
| 4,574,264 | 3/1986 | Takahashi et al. .......................... 422/98 |
| 4,587,172 | 5/1986 | Roy et al. .......................... 428/450 |
| 4,703,023 | 10/1987 | Yamai .......................... 501/102 |
| 4,718,991 | 1/1988 | Yamazoe et al. .......................... 204/1 |
| 4,751,206 | 6/1988 | Yamai et al. .......................... 501/102 |
| 4,938,928 | 7/1990 | Koda et al. .......................... 422/98 |
| 4,961,957 | 10/1990 | Kawae et al. .......................... 427/125 |
| 4,976,991 | 12/1990 | Ammenile et al. .......................... 427/125 |
| 5,133,857 | 7/1992 | Alberti et al. .......................... 204/425 |
| 5,393,404 | 2/1995 | Greenblatt et al. .......................... 204/430 |

OTHER PUBLICATIONS

Zircuniom Phosphate Membranes for InterMediates Temperatures Fuel Cells, C Berger and M.P. Strier, vol. 115, No. 3, Mar., 1968

*Primary Examiner*—T. Tung
*Attorney, Agent, or Firm*—Friscia & Nussbaum

[57] ABSTRACT

A humidity sensing device comprising a solid electrolyte evidencing proton conductivity includes $HZr_2P_3O_{12}$ or a composite comprising $HZr_2P_3O_{12}/ZrP_2O_7$. The humidity sensing device is operative over a temperature range from 350°–600° C. The humidity sensor is operated by an impedance-type cell.

9 Claims, 14 Drawing Sheets

1

IMPEDANCE TYPE HUMIDITY SENSOR WITH PROTON-CONDUCTING ELECTROLYTE

RELATED APPLICATIONS

This application is a continuation-in-part application of U.S. patent application Ser. No. 08/079,237, filed Jun. 17, 1993, which issued on Feb. 28, 1995 as U.S. Pat. No. 5,393,404, the entire disclosure of which is incorporated herein by reference.

BACKGROUND OF THE INVENTION

1. Field of the Invention

The present invention relates to a humidity sensing device comprising a solid electrolyte. More particularly, the present invention relates to an impedance type humidity sensing device comprising a solid electrolyte evidencing proton conductivity.

2. Description of the Prior Art

Heretofore, the use of solid electrolyte humidity sensors as a means for monitoring or controlling the environment has been limited. These devices typically provide an electrical signal which may be potentiometric, amperometric or conductometric in nature in response to the level of humidity in the atmosphere. Among the devices proposed for this purpose are the galvanic cell type humidity sensors which either employ proton or oxide ion conducting electrolytes as humidity sensing elements. Additionally, impedance type humidity sensors may be employed for this purpose. The electromotive force evidenced by such cells typically follows Nernstian behavior which serves as a calibration curve for the sensor. The proton or oxide ion conducting solid electrolyte chosen for use in such devices then becomes the prime factor in the construction of such humidity sensors. Workers in the art selected sintered perovskite-related phases in the barium or strontium cesium yttrium oxide family ($MCe_{1-x}Y_xO_3$ [M=Ba or Sr]) for this purpose. However, studies have revealed that electronic and/or proton ion conduction in these materials results in significant deviations from Nernstian behavior, so imposing additional calibration requirements. Accordingly, workers in the art have focused their interest upon alternative materials in their quest to find humidity sensing properties which will satisfy their needs, particularly those which are operative at high temperatures in excess of 100° C.

Numerous references disclose gas sensors and humidity sensitive devices. However, none of these references disclose or suggest the specific galvanic type sensor described herein. Typical of the prior art references are the following:

Nakamura et al., U.S. Pat. No. 4,024,036, discloses a proton permselective solid-state member formed of a heteropoly acid represented by the generic formula, $H_m[X_xY_yO_z]nH_2O$ or a salt thereof. In this formula, X represents at least one member selected from the group consisting of boron, aluminum, gallium, silicon, germanium, tin, phosphorous, arsenic, antimony, bismuth, selenium, tellurium, iodine and the first, second and third transition metals, Y represents at least one member selected from the first, second and third transition metals, provided that X and Y do not represent the same substance, m, x, y, z and n each represents a positive numerical value. The permselective member can be used as an electrolyte in a fuel cell and as a membrane in a hydrogen gas refining system.

Murata, et al., U.S. Pat. No. 4,497,701 discloses a humidity sensitive device comprising an insulated substrate, first and second electrodes formed on the surface of the insulating substrate and spaced apart from each other, and a humidity sensitive film formed on the surface of the insulating substrate and covering the surface of the substrate between the electrodes. It includes a conductive powder or a semi-conductive powder, a solid electrolyte powder and an organic polymer, at least part of which is cross-linked by a zirconium compound, which serves as a cross-linking agent to form a bridge to the organic polymer and to make the structure of the humidity sensitive film stable. Additionally, the zirconium compound increases the variation rate of the resistance value as a function of moisture absorption. Thus, the range of the resistance value can be made large and the humidity sensitive device can be used as a dew sensor.

Roy et al., U.S. Pat. No. 4,587,172 discloses a low expansion ceramic material having the molecular formula $i(Na)j(Zr_{2-z}Na_{4z}) k(P_{3-x}Na_xSi_x) O_{12}$. This composition evidences a low thermal expansion and may be used in low expansion optical reflective structures. Such structures have an optically reflecting film deposited on a ceramic substrate having a very small thermal coefficient of expansion.

Yamai, U.S. Pat. No. 4,751,206, discloses a method of making a low thermal-expansive zirconyl phosphate ceramic, $(ZrO)_2$—$P_2O_7$. The method involves sintering a fine-powder compact of zinc oxide, magnesium oxide, bismuth oxide, manganese oxide, iron oxide, cobalt oxide, or nickel oxide, at a temperature ranging from 1200° C. to 1700° C. The resulting ceramic has a low thermal expansion coefficient.

Yamazoe, et al., U.S. Pat. No. 4,718,991, relates to proton gas sensors and a method for the use thereof in detecting gasses in oxygen containing ambients. The described sensor comprises three electrodes, an ionization electrode, a reference electrode and a detection electrode, each of which is connected to a proton conductor. Upon short circuiting of the ionization and reference electrodes, a measurement of the difference of potential across the detection electrode is made, thereby indicating the presence of gas.

Yamai, et al., U.S. Pat. No. 4,751,206, discloses a low thermal expansion material, potassium zirconium phosphate. This material has high strength and high thermal shock resistance. This product may be used for furnace refractories which are subject to thermal shock and as thermal shielding materials such as protective tiles on space vehicles which shield the vehicle from the heat of re-entry to the atmosphere.

Kawae, et al., U.S. Pat. No. 4,961,957, discloses an electrochemical cell having a solid electrolyte body and a plurality of electrodes formed thereon. At least one of the electrodes is porous, for use in determining the concentration of a subject gas in an atmosphere. The porous electrode may be comprised of platinum, an alloy of platinum, or another metal such as nickel, silver, gold, rhodium, palladium, iridium or ruthenium. The solid electrolyte body used as an oxygen sensor is formed of an oxygen-ion conductive solid electrolyte which includes $ZrO_2$ (zirconia) as a major component, and at least one additive such as $Y_2O_3$, $CaO$, $Yb_2O_3$, and $MgO$.

Ammende et al., U.S. Pat. No. 4,976,991, discloses a hydrogen sensor having a solid electrolyte comprised of nasicon, titsicon, khibinskite, wadeite or $\beta$-$Al_2O_3$. The electrodes are formed of platinum, palladium or palladium oxide.

U.S. Pat. No. 3,276,910 to Grasselli, et al. discloses an ion transfer medium for an electrochemical reaction apparatus for converting chemical energy into electrical energy. The invention employs a solid ion transfer medium. The device includes a non-conductive housing, with a solid ion-exchange membrane of a polymeric salt of a Group IV metal in an acid selected from the group consisting of phosphoric and arsenic acids positioned within the housing, electrodes positioned on the solid ion exchange membrane, means for introducing a gaseous fuel into contact with one side of the membrane, and means for introducing an oxidant onto the other side of the membrane and electrical conductors extending from the electrodes to the exterior of the housing.

U.S. Pat. No. 5,133,857 to Alberti, et al. discloses a solid-state sensor for determining the concentration of gases that can react with hydrogen. The device includes a solid-state proton conductor having a reference electrode on one side thereof and an electrode which catalyses the reaction of the gas to be detected. The sensor is connected to a power feed system which supplies a current or voltage impulses. Also included is a system which detects the value of the potential after each impulse. This device can be operated at room temperature.

Alberti, et al. discloses an oxygen conductor, not a proton conductor. The specific composition of this oxygen conductor is described as zirconium hydrogen phosphate or zirconium triphosphate doped with silicates, such as $H_3Zr_2PO_4(-SiO_4)_2$ (column 2, lines 57–60).

OBJECTS AND SUMMARY OF THE INVENTION

An object of the present invention is to prepare a humidity sensor capable of operating at elevated temperatures.

A further object of the invention is to provide a galvanic cell type humidity sensor operative at temperatures in excess of 100° C.

Another object of this invention is to provide a humidity sensor based upon proton conductivity.

Still another object of this invention is to provide a humidity sensor evidencing high levels of reproducibility and durability.

Another object of the present invention is to provide a proton conducting solid electrolyte appropriate for humidity sensing at relatively high temperature.

Another object of the invention is to provide a proton conducting solid electrolyte humidity sensor that is selective (i.e. does not give a response when impurity gases such as ethyl alcohol, acetic acid and ammonia are present).

It is even another object of the present invention to provide a humidity sensing device based on an impedance type response.

It is yet another object of the present invention to provide an impedance type humidity sensor with applications in automatically controlled systems.

It is even a further object of the present invention to provide a humidity sensing device with an all-ceramic material "MACOR".

It is still a further object of the present invention to provide a humidity sensor based on films of functionally gradient materials.

It is an additional object of the present invention to provide a humidity sensor employing film technology wherein the protonic\oxide ion conductivities of the materials employed can be varied.

It is even an additional object of the present invention to provide miniaturized pH sensing membranes for in-situ pH sensing applications in food processing.

In accordance with the present invention these objectives have been attained while effectively obviating the limitations of the humidity sensitive devices employed heretofore.

The present invention comprises a humidity sensing device based upon a protonic Nasicon conductor comprising a galvanic cell based upon a $HZr_2P_3O_{12}/ZrP_2O_7$ composite humidity sensor operative in the range of 350°–600° C. The described sensor evidences Nernstian behavior which confines the mechanism of proton conductivity in the composite electrolyte sensor.

In another embodiment of the present invention, the humidity sensing device comprises an impedance type cell based upon a $HZr_2P_3O_{12}/ZrP_2O_7$ composite.

BRIEF DESCRIPTION OF THE DRAWINGS

The invention will be more readily understood by reference to the following detailed description taken in conjunction with the drawings wherein.

DETAILED DESCRIPTION OF THE INVENTION

The first step in the fabrication of the humidity sensor of the present invention involves preparing a $HZr_2P_3O_{12}/ZrP_2O_7$ composite. The proton substituted NASICON, $NaZr_2P_3O_{12}$, is obtained by the conventional technique of calcination of $(NH_4)Zr_2P_3O_{12}$, the latter being conveniently synthesized hydrothermally in an autoclave lined with polytetrafluoroethylene. This technique typically involves reacting an aqueous mixture of $ZrOCl_2 \cdot 8H_2O$ and $NH_4H_2PO_4$. Crystallization of the mixture is then effected under autogenous pressure and the resultant crystalline product is filtered, washed and dried at ambient temperature. Thereafter, $HZr_2P_3O_{12}$ is prepared by heating the crystalline $(NH_4)Zr_2P_3O_{12}$ in air at approximately 650° C. for 5 hours. The other starting material $\alpha\text{-}ZrP(Zr[HPO_4]_2 \cdot H_2O)$ is synthesized by conventional techniques.

Next, $HZr_2P_3O_{12}$ (HZP) in powdered form is mixed with $\alpha\text{-}Zr(HPO_4)_2 \cdot H_2O$ (ZrP) in a mole ratio of unity to yield an HZP-ZrP mixture. The resultant mixture is then ground and pelletized, typically with a pressure of 150 klb/in² to yield a dense ceramic pellet. The resultant humidity sensing element is a sintered compact composite phase of $HZr_2P_3O_{12}$ and $ZrP_2O_7$ which is mechanically stable.

The resultant pellet is next sintered in air to yield a pellet having a density greater than 80% of ideal density.

The next step in the fabrication of the inventive humidity sensor involves forming electrode connections on the sintered pellet. This end is attained by coating each face of the pellet with platinum ink. Finally, the pellet, bearing platinum electrodes, is heated at approximately 600° C. for a time period of the order of 10 hours to form the desired sensor disk.

Figure 1A:
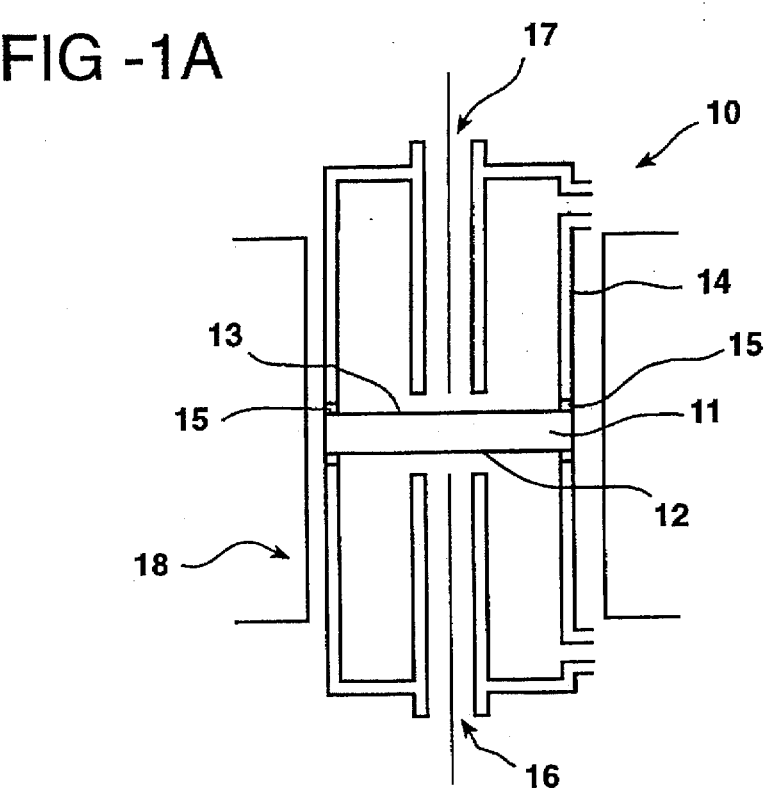
FIG. 1a and FIG. 1b are schematic representations of a galvanic type humidity sensor of the invention.

With reference now to FIG. 1A, there is shown a schematic representation of a galvanic cell 10 in accordance with the invention. Shown in FIG. 1a is a sensor electrolyte 11 comprising a $HZr_2P_3O_{12}/ZrP_2O_7$ composite humidity sensor having platinum electrodes 12 and 13 affixed thereto. Electrolyte 11 is shown disposed within quartz tubing 14 at essentially the midpoint thereof and held in place by means of ceramic sealant 15, thereby dividing the cell into two chambers, a reference gas chamber 16 and a sample gas chamber 17. In operation, cell 10 is disposed within an electric furnace 18 and humidity is introduced to reference chamber 16 and sample chamber 17 from a suitable water reservoir (not shown) using air as the carrier gas at a flow rate typically of the order of 220 cc/min. For comparative purposes, the humidity in the reference compartment is fixed at 3.16 mmHg by maintaining the reference water reservoir in an ice bath. The humidity in the sample compartment is varied by altering the temperature of the sample water reservoir.

Figure 1B:
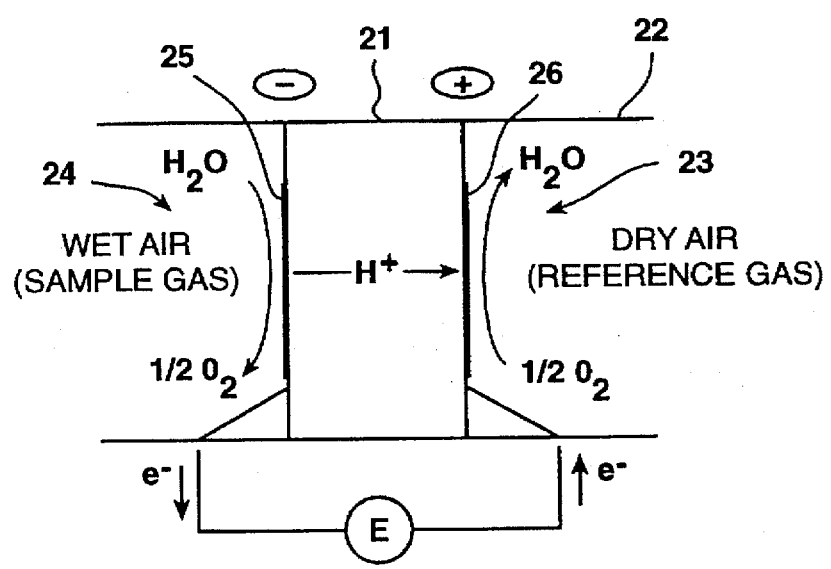

With reference now to FIG. 1b, there is shown a schematic representation of a galvanic cell assembly of the invention. Shown is proton conducting solid electrolyte 21 disposed in chamber 22 which separates the cell into reference gas chamber 23 and sample gas chamber 24. When the water vapor in chambers 23 and 24 is different, the following reactions occur at electrodes 25 and 26, respectively:

 (anode)  Equation [1]

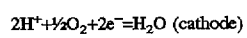 (cathode)  Equation [2]

The equilibrium partial pressure of water in the galvanic cell is expressed by the Nernst equation:

$$E = RT/2F \ln [P_{H_2O}(P^r{}_{O_2})^{1/2}/P^r{}_{H_2O}(P_{O_2})^{1/2}] \quad \text{(Equation [3])}$$

$$P_{H_2O} = P^r{}_{H_2O} \cdot (P_{O_2}/P^r{}_{O_2})^{1/2} \exp(2EF/RT) \quad \text{Equation [4]}$$

wherein $P^r{}_{H_2O}$ and $P^r{}_{O_2}$ represent the partial pressures of water and oxygen, respectively, at the reference electrode 26, E is the electromotive force of the electrolyte, F is the Faraday constant and R is the gas constant. Under ambient conditions, $P_{O_2}$ is assumed to be equal to $P^r{}_{O_2}$ and for sensing applications the partial pressure of water vapor in the sample gas, $P_{H_2O}$ can be estimated from the electromotive force of the cell in accordance with the following equations:

$$E = RT/2F \ln (P_{H_2O}/P^r{}_{H_2O})$$

$$P_{H_2O} = P^r{}_{H_2O} \cdot \exp(2EF/RT)$$

Figure 1C:
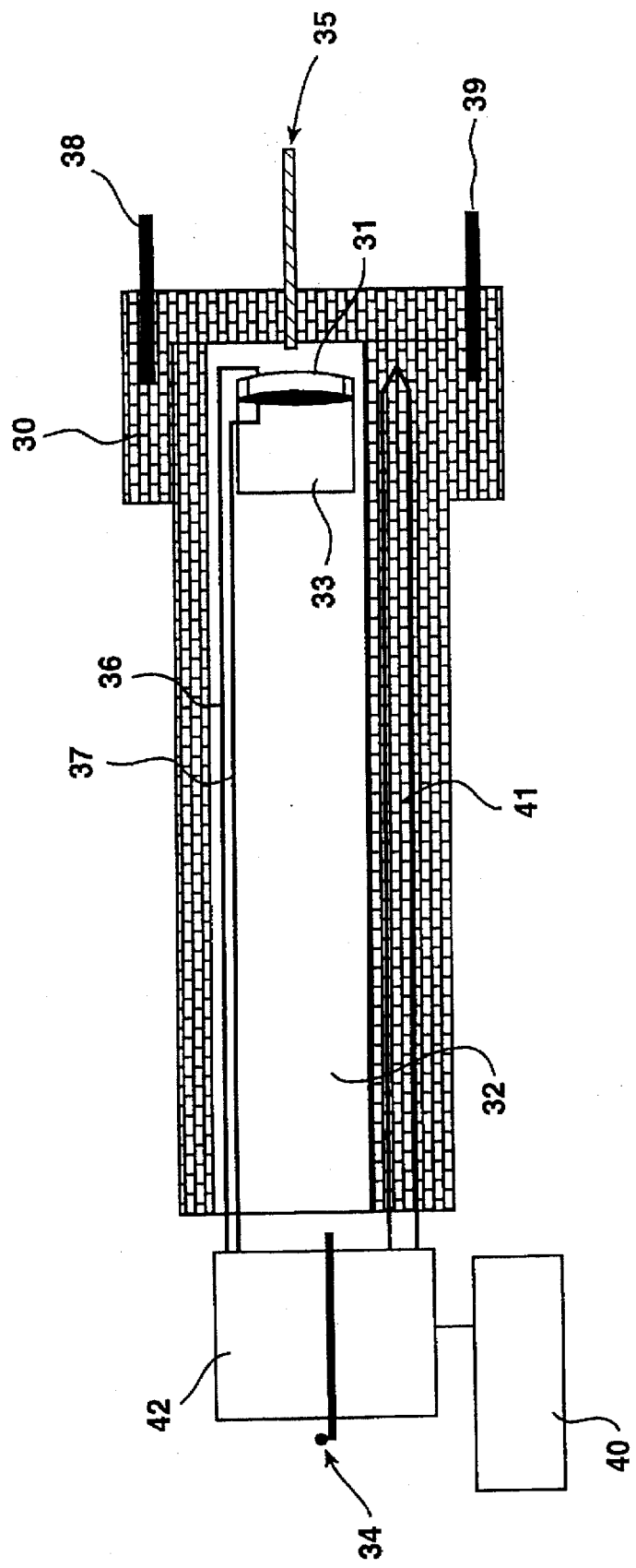
FIG. 1c is a front elevational view in cross section of a ceramic humidity probe in accordance with the invention.

With reference now to FIG. 1c, there is shown a front elevational view in cross-section of a ceramic humidity probe in accordance with the present invention. Shown is MACOR block 30 having a proton conducting solid electrolyte sensor 31 comprising a $HZr_2P_3O_{12}/ZrP_2O_7$ composite disposed in MACOR tube 32 and held in place by means of an alumina ring 33. Conduits 34 and 35 are used for the introduction of reference and sample gases, respectively, into tube 32. Sensor 31 is connected to platinum leads 36 and 37. Also shown connected to block 30 are cartridge heaters 38 and 39. Output meter 40 is connected to signal processor 42 which is connected to platinum leads 36 and 37 and to a thermocouple 41 which is disposed in block 30.

In operation, block 30 is heated by means of heaters 38 and 39 and humidity is introduced through the reference and sample gas conduits 34 and 35, respectively, from a suitable source. Humidity is monitored by means of an output meter 41.

Figure 2:
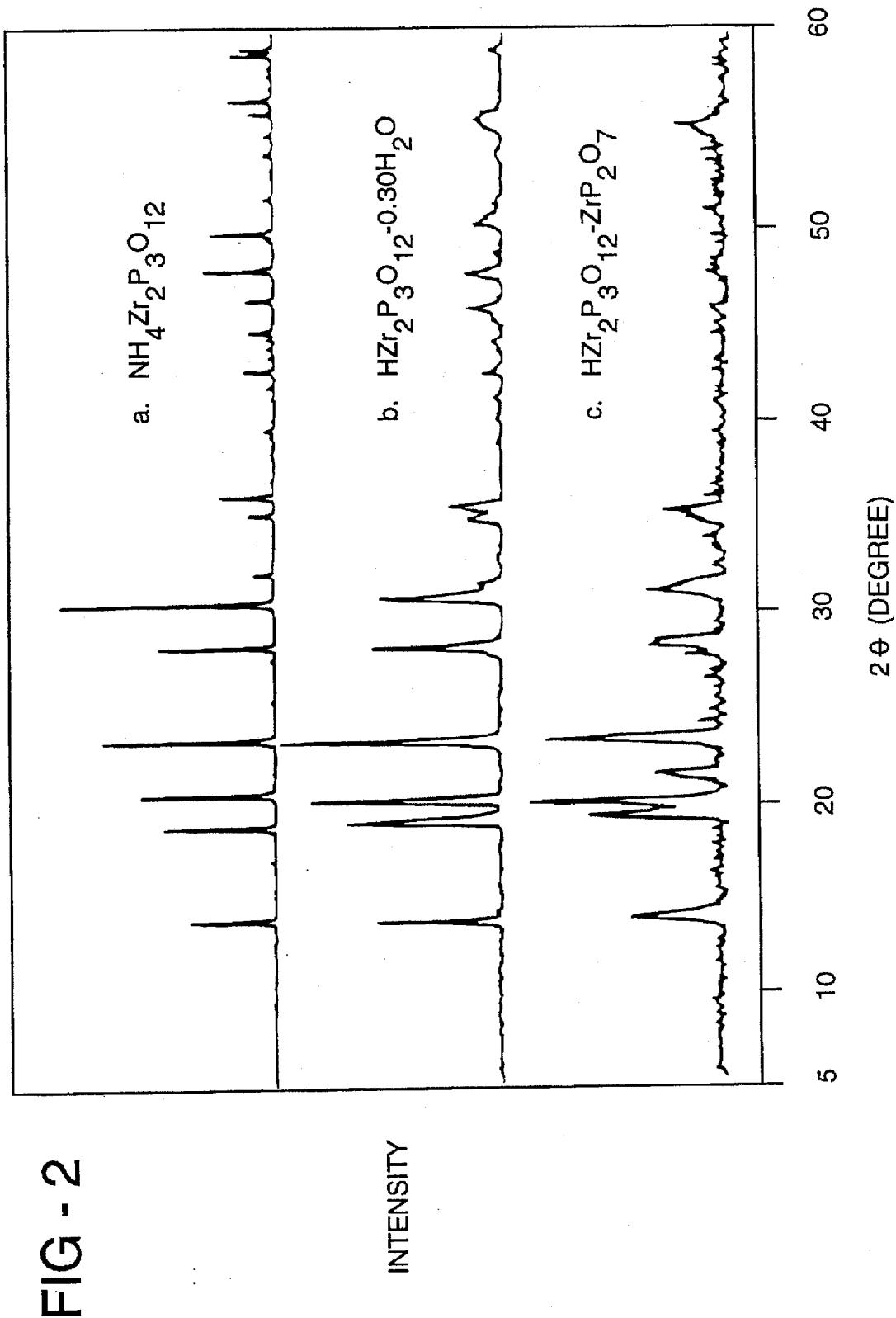
FIG. 2 is a graphical representation on coordinates of relative intensity against 2θ in degrees showing x-ray diffraction patterns of (a) pure $(NH_4)Zr_2P_3O_{12}$, (b) $HZr_2P_3O_{12}$ and the sensor material $HZr_2P_3O_{12}/Zr_2P_3O_7$.

With reference now to FIG. 2, there is shown a graphical representation on coordinates of Intensity against 2θ in degrees comparing x-ray diffraction patterns of $(NH_4)Zr_2P_3O_{12}$, $HZr_2P_3O_{12} \cdot 0.3H_2O$ and the $HZr_2P_3O_{12}/ZrP_2O_7$ composite sensor material of the invention. As noted in FIG. 2a, hydrothermally synthesized $(NH_4)Zr_2P_3O_{12}$ evidences high crystallinity and a structure identical with that of high temperature NASICON which evidences two polymorphs which are dependent upon calcination temperature. Below 600° C. a triclinic phase appears, and above 600° C. a rhombedral phase appears, the latter not undergoing a phase transition upon cooling or heating. Both phases respond to changes in humidity; however, the rhombohedral phase was used as the starting material for the sensor because of its stability at high temperature. The x-ray diffraction pattern of the sensor material of the invention (FIG. 2c) is identical with that of rhombohedral $HZr_2P_3O_{12}$ but for a few peaks attributable to $ZrP_2O_7$, thereby confirming the material as a composite of $HZr_2P_3O_{12}$ and $ZrP_2O_7$.

Figure 3:
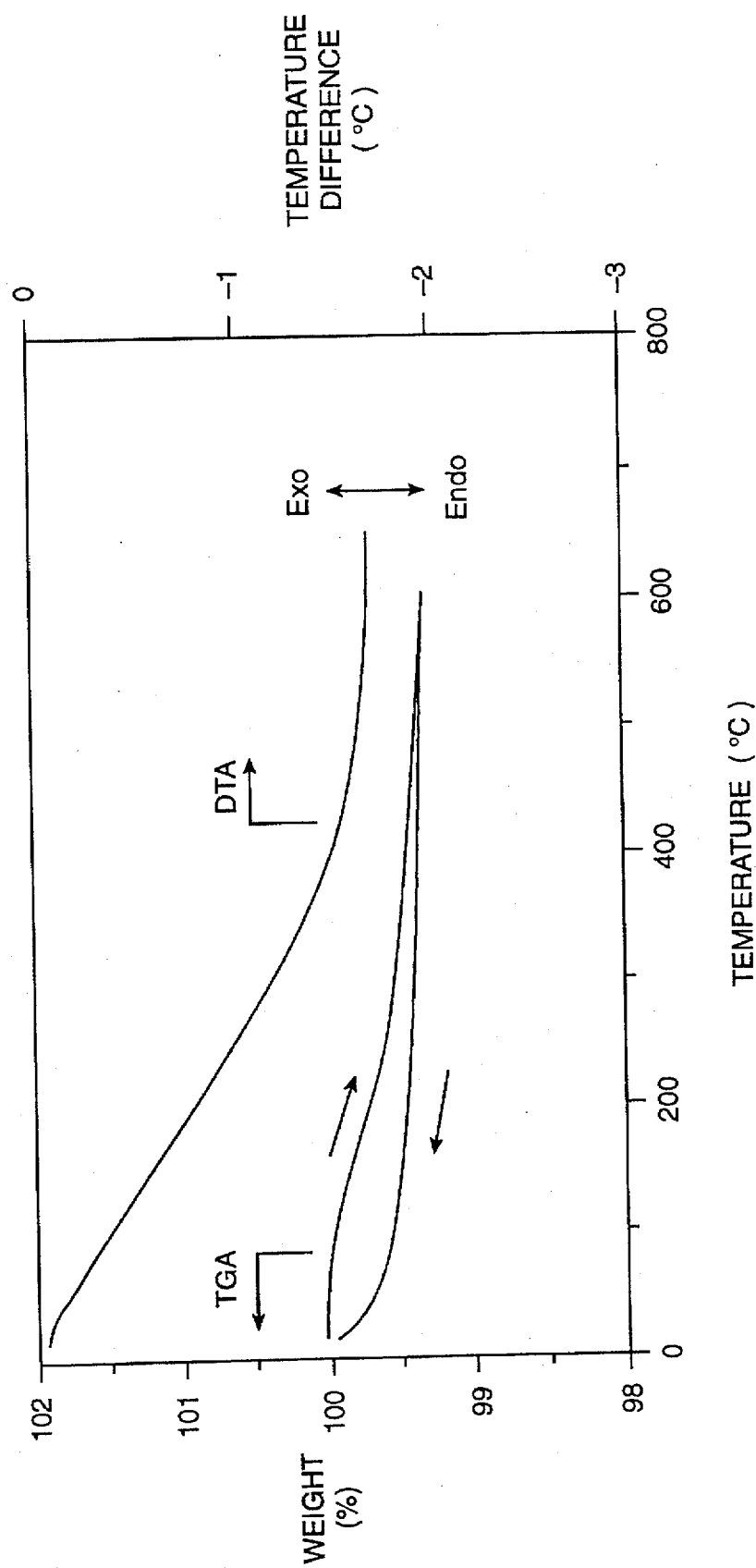
FIG. 3 is a graphical representation on coordinates of weight percent against temperature in degrees Centigrade showing the DTA and TGA curves for the described sensor material.

With reference now to FIG. 3, the DTA and TGA curves for a sample of the sensor material of the invention is shown in graphical form on coordinates of weight against temperature in degrees centigrade. No phase change is evident over the temperature range (approximately 0°–600° C.), so indicating that the material is thermally stable during a heating/cooling cycle. It is noted that the DTA curve slopes smoothly during the entire period of heating, so indicating a gradual endotherm. The TGA heating curve reveals that upon heating a weight loss of approximately 0.75% occurs which is attributable to water loss which is absorbed by the sensor on exposure to air which corresponds with the formulation $HZr_2P_3O_{12} \cdot ZrP_2O_7 \cdot 0.15H_2O$. The TGA cooling curve for the same sample evidenced a weight gain beginning at approximately 400° C. due to absorption of water at relatively low temperature.

Figure 4:
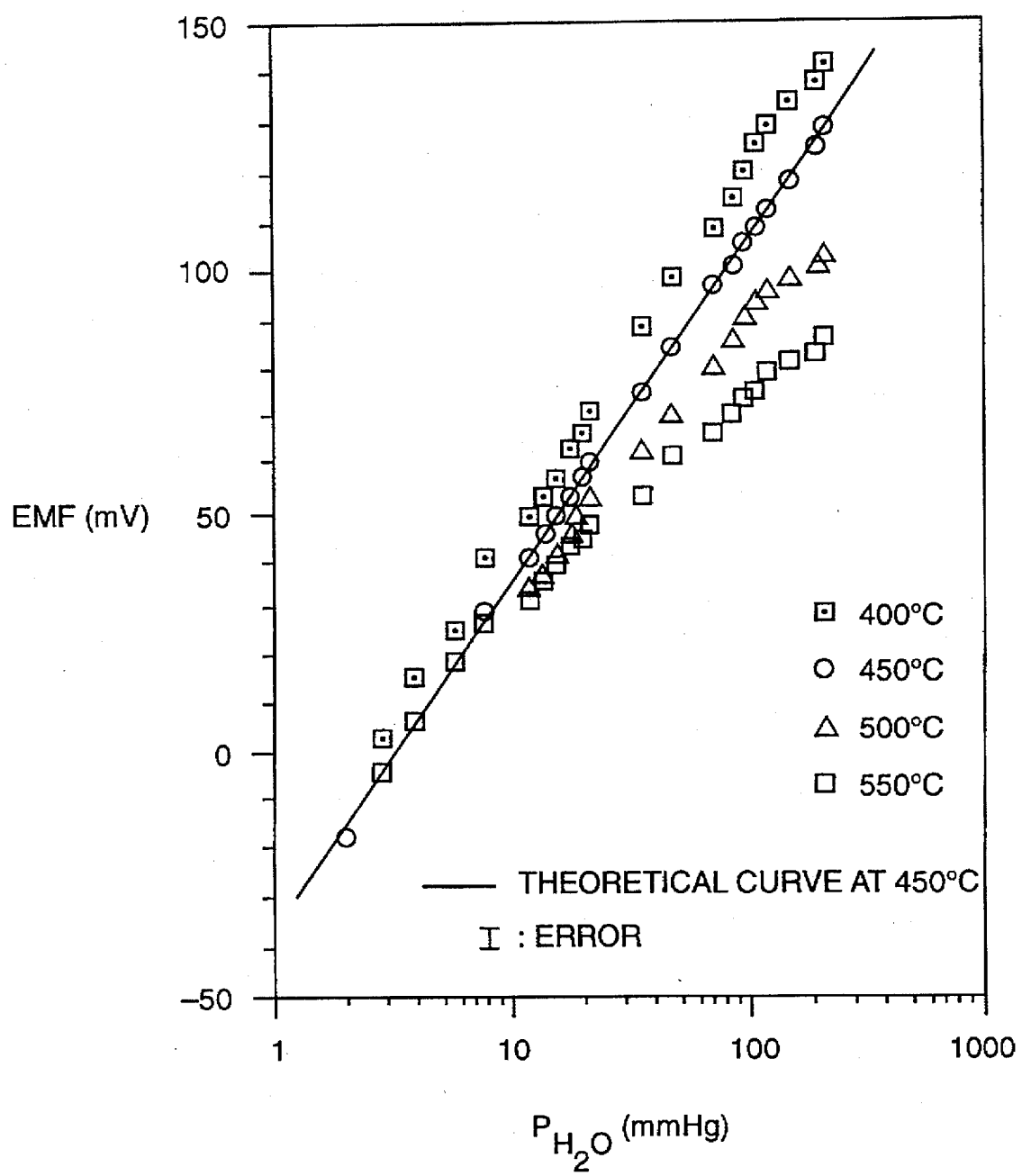
FIG. 4 is a graphical representation on coordinates of electromotive force in millivolts against water vapor pressure, P in mmHg, showing the humidity dependence of electromotive force of the sensor at 400°, 450°, 480°, 500° and 550° C. respectively.

With reference now to FIG. 4, there is shown the electromotive force (EMF) response of the galvanic cell as a function of the log of the partial pressure of water in the sample compartment at a temperature within the range of 400°–550° C. The Figure reveals that at temperatures less than 450° C. the EMF values are higher and at temperatures greater than 450° C. the EMF values are lower than expected from the Nernst equation and are non-linear. This voltage variation at the lower temperatures is attributed to absorption of water on the surface of the sensor disk which is confirmed by the TGA cooling curve shown in FIG. 3.

Figure 5:
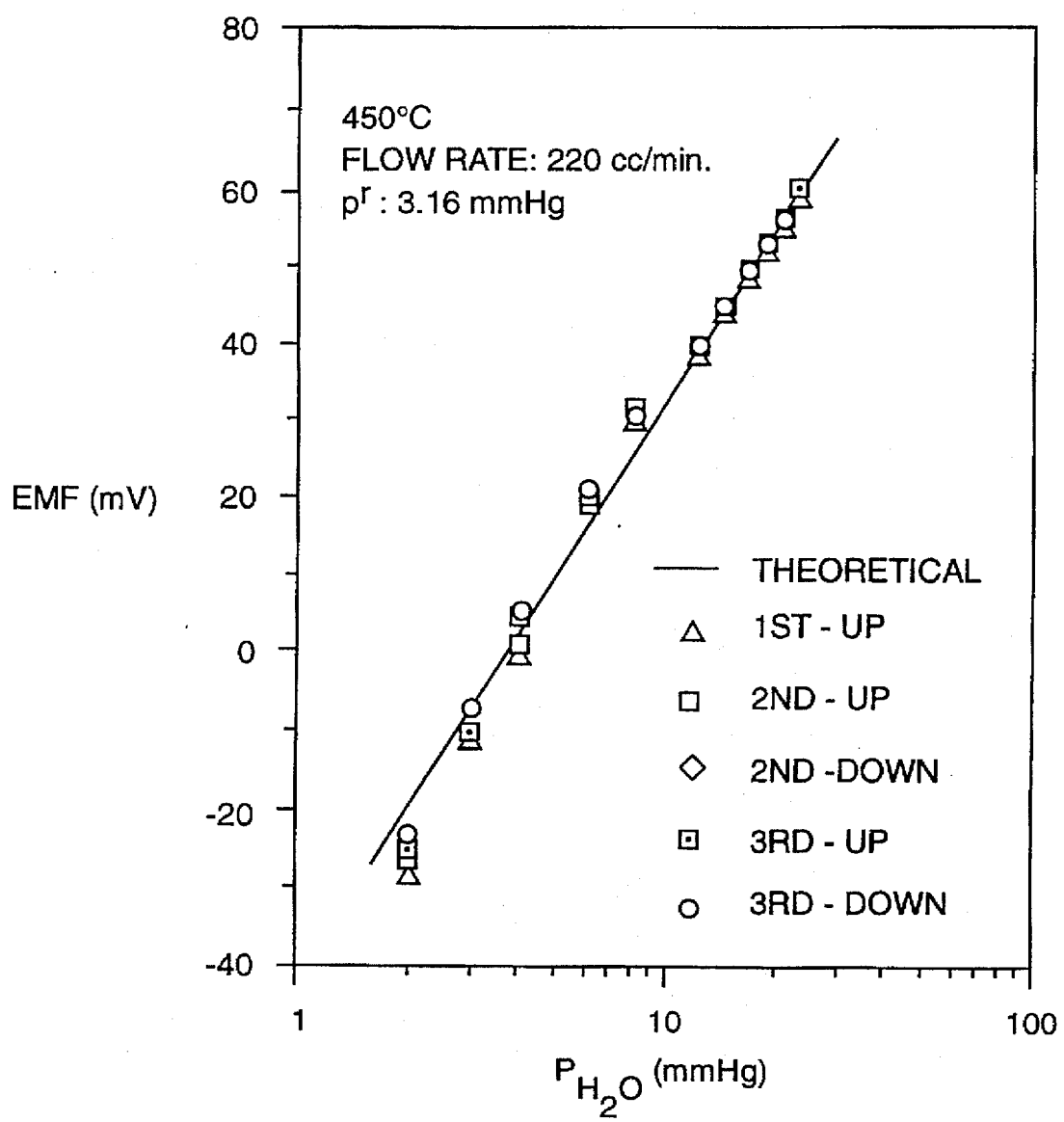
FIG. 5 is a graphical representation on coordinates of electromotive force in millivolts against water vapor pressure, P, in mmHg showing the humidity dependence of electromotive force (EMF) of the sensor of the invention at 450° C. showing cycling data.

The conduction characteristics of the sensor material were also studied using a wet oxygen concentration cell having the same partial pressure of water vapor in both the sample and reference compartments. The partial pressures of oxygen in both the sample and reference compartments were adjusted from 68 to 745 mmHg with helium used as a balancing gas. The measured EMFs at 450° C. of the wet oxygen concentration cell with changing oxygen concentration shown in FIG. 5 follow the theoretical values calculated from Equation 3. This confirms that the described sensor operates in the cell by a mechanism conforming to the Equations, 1 and 2.

A similar experiment performed in a wet hydrogen concentration cell evidenced Nernstian behavior as a function of the ratio of hydrogen partial pressure in the reference and sample compartments ($H_2'/H_2''$). This indicated that under the appropriate wet conditions in both chambers, the device will operate as an oxygen sensor.

Figure 6:
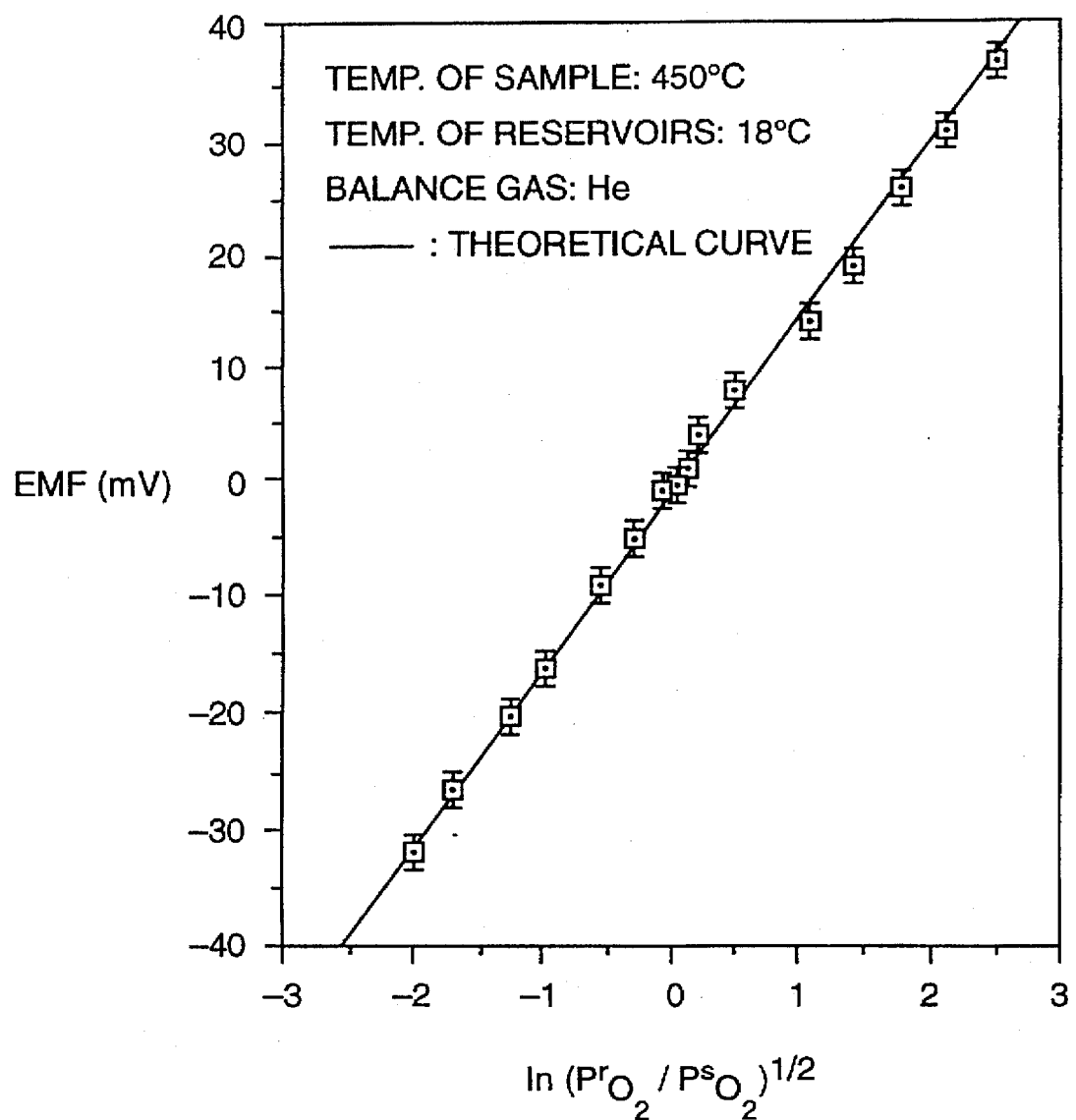
FIG. 6 is a graphical representation on coordinates of EMF in millivolts against the ratio of partial oxygen pressures in the reference and sample compartments showing conduction characteristics of the sensor material.

FIG. 6 is a graphical representation on coordinates of electromotive force (EMF) in millivolts against the ratio of the partial pressure of oxygen in the reference and sample compartments. This figure is indicative of the conduction characteristics of the sensor material. A wet oxygen concentration cell with the same partial pressures of water vapor in both the sample and reference compartments was employed. Pressures in these compartments were adjusted with a helium balance gas from 68–745 mmHg. At 450°, the measured electromotive forces of the wet oxygen concentration cell with changing oxygen concentration follow the theoretical values calculated from Equation 3 and noted by reference to FIG. 6, so confirming that the sensor material operates by a mechanism in accordance with Equations 1 and 2.

Figure 7A:
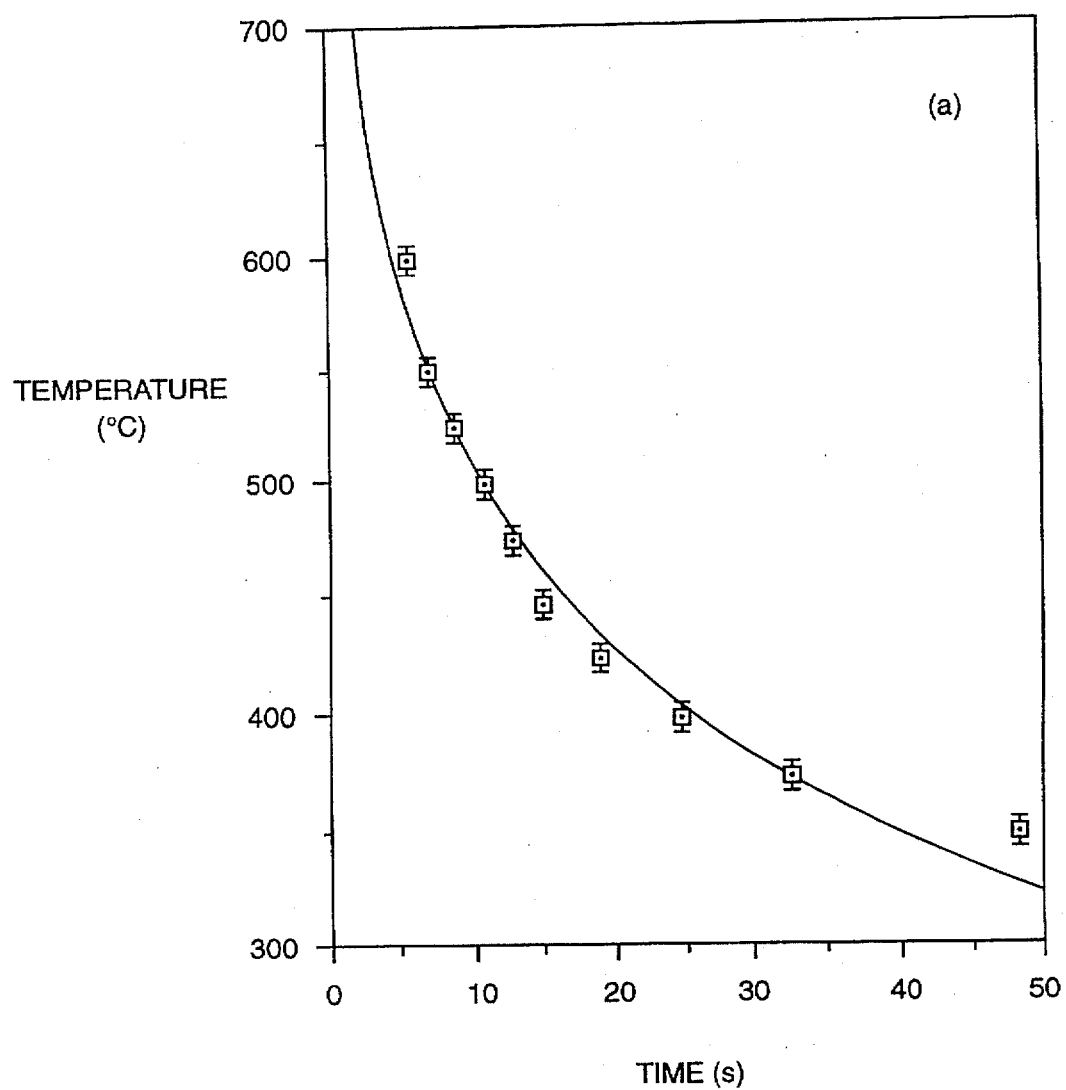
FIG. 7a is a graphical representation on coordinates of temperature in degrees Centigrade against time in seconds showing the temperature dependence of the response time for the humidity sensor with a change of partial pressure of water from 6–8 mmHg.
Figure 7B:
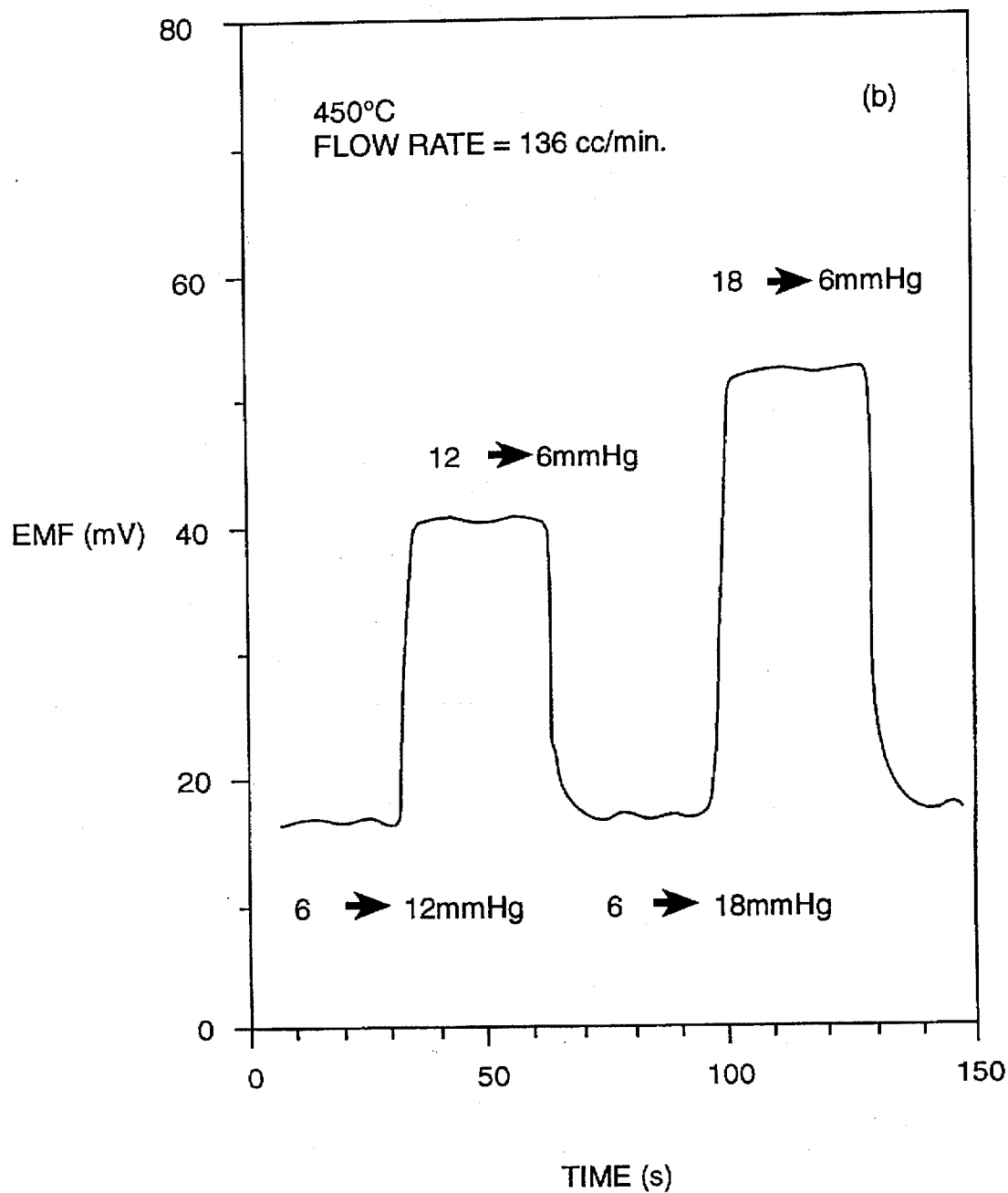
FIG. 7b is a graphical representation on coordinates of electromotive force against time in seconds showing the variation of electromotive force with time for the same cell as shown in FIG. 7a with partial pressure changes ranging from 6–12 mmHg and 6 to 18 mmHg at 450° C.

The response time of the sensor as a function of temperature on changing water vapor pressure is shown in FIG. 7a. As the humidity varies, the EMF responds rapidly and reaches a steady state within a few seconds at all temperatures studied. At 350° C., the response time was 48 seconds. However, at elevated temperatures, for example 450° C., the response time was only 15 seconds, as noted in FIG. 7b.

The effect of selected impurity gases in the water vapor was also studied. Thus, for example, ethyl alcohol, acetic acid and ammonia were introduced to the system and the EMF of the sensor evaluated. Pure ethyl alcohol, acetic acid and ammonia, respectively, were mixed with water in a volume ratio of 100 ppm or 1000 pm. The solution mixture served as the source of saturated water vapor plus impurity vapor supplied to the sample compartment. The sensor material was found to be stable with respect to each of the impurity gasses and humidity sensing was not affected within the experimental error of measurement for 100 ppm impurity gas concentration. This evidences the selectivity of the sensor. As the concentration of impurity gas increased beyond 100 ppm, the EMF value also increased. At this temperature, the EMF appears to be dependent upon the ethyl alcohol concentration at values greater than 100 ppm. This phenomenon is attributed to proton reactivity of the ethyl alcohol molecules which are absorbed on the surface of the sensor disk in the sample compartment which provides additional protons and enhanced EMF, so suggesting the use of the humidity sensor as a proton-containing gas sensor and/or catalyst.

In another embodiment of the present invention, the humidity sensor may be based on an impedance cell type. The humidity sensor of this embodiment is based on impedance type response to changing humidity conditions of a proton conducting solid electrolyte.

The impedance type humidity sensor is also based on a NASICON composite material, $HZr_2P_3O12\text{-}ZRP_2O_7$. This device is designed for sensing humidity at temperatures exceeding 100° C. The device may be fabricated from an all ceramic composite MACOR.

Figure 8:
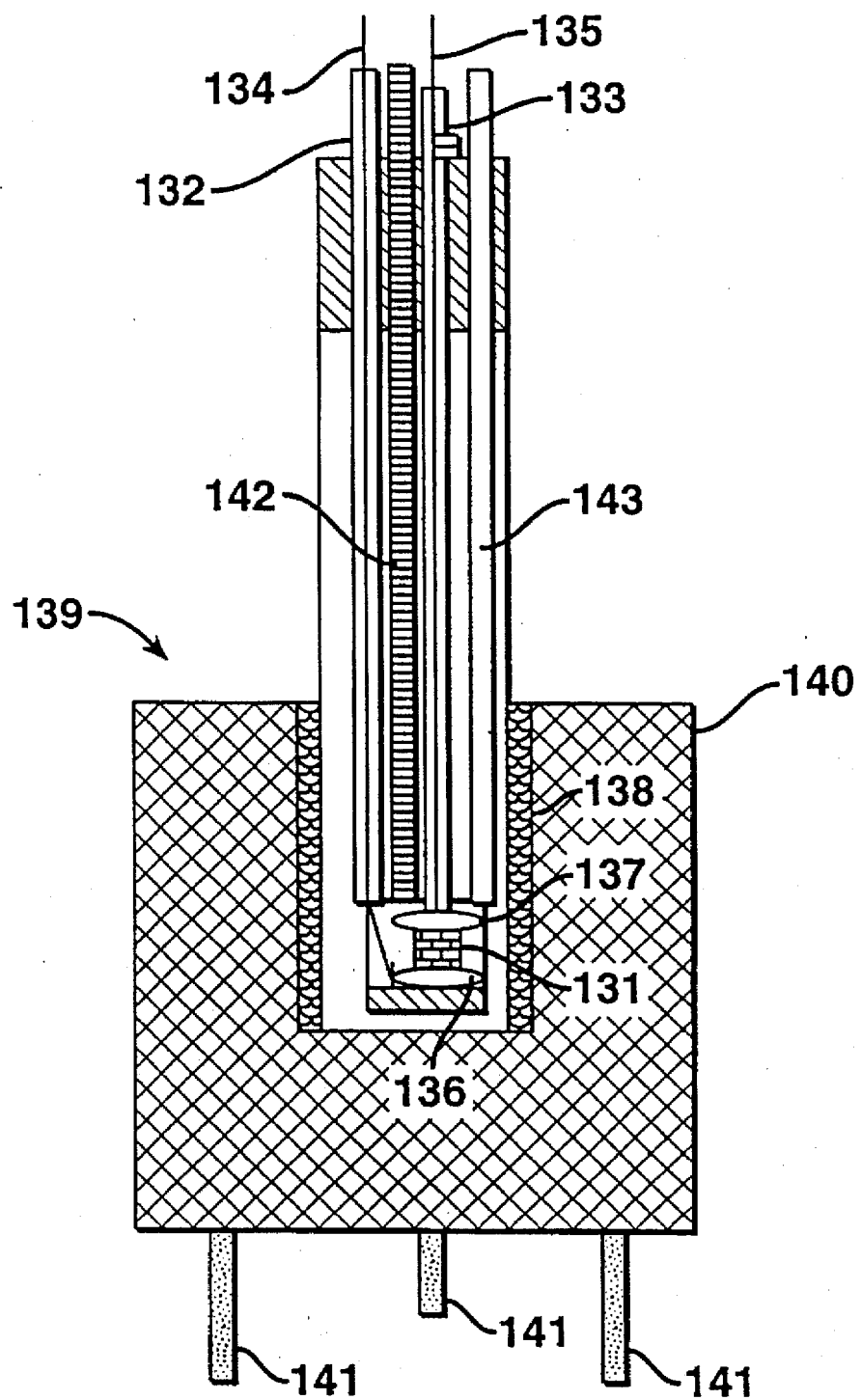
FIG. 8 is a schematic representation of another embodiment of the humidity of the present invention wherein the sensor is based upon an impedance cell type.

As shown in FIG. 8, the sensor 131 is connected to platinum electrodes 136 and 137 which are interconnected with electrode leads 134 and 135 which run from the electrodes 136 and 137 through conduits 132 and 133. The sensor 131 and electrodes 136 and 137 are disposed within furnace core 138 of furnace 139 which includes insulation 140 and which is supported by legs 141. The furnace 139, like the cartridge heaters referred to in respect to the galvanic cell type sensor, heats the sensor to its operating temperature. A thermocouple 142 extends to the sensor 131 and a sample gas is introduced to the sensor through conduit 143. This embodiment of an impedance type cell is only but one example of an impedance based humidity sensor, and other configurations of an impedance type cell are considered within the scope of the present invention.

The results obtained with this composite are reproducible for humidity sensing at temperatures in the range of 200°–500° C. in both impedance and e.m.f. modes of operation. This device provides excellent response time to changing humidity conditions. However, during prolonged operation at 450° C., the metal covered cartridge heating elements may react with the ceramic material into which they are housed, resulting in a breakdown of the sensor operation primarily due to the un-matched thermal expansion coefficients of the metal and the ceramic. In addition, a need for a reference gas in the operation of e.m.f. type design was a concern.

In this impedance-type humidity sensing device, the sensor is heated uniformly with an external furnace. This embodiment, unlike the previous EMF-type, is based on the humidity-dependant impedance of the sensor and therefore does not require reference humidity for its operation. The impedance type sensing characteristics of the $HZr_2P_3O12\text{-}ZRP_2O_7$ composite have been previously established herein.

The sensors developed for impedance type response are proton conducting solid electrolytes.

The operative device may be integrated with custom designed electronic circuitry and software installed on a computer, which is used in the measurement of the impedance of the sensor.

In view of problems such as excessive local heating and corrosive attack of the cartridge type contact heaters on the MACOR, it is desirable to have an external furnace assembled with heating elements to provide uniform heating in the sensing area. The temperature of the furnace is controlled with a thermocouple positioned at the sensor.

In this embodiment of the device, the sensor element can be maintained at 450° C. in a cavity drilled into the MACOR block. The heating of the ceramic block is achieved by means of cartridge type heating elements.

The all-ceramic construction significantly minimizes the heat transfer between the furnace and processing ends of the device. Accordingly, significant improvement in the size of the device has been achieved and the water cooled jacket near the signal-processing end was eliminated.

Another advantage of the new design is that the sensor element can be assembled separately by sandwiching the composite pellet between a pair of alumina o-rings using a high temperature ceramic adhesive. Thus incorporation of a new sensor element into the device is fairly easy minimizing the down-time required for maintenance.

The stability of the prototype for continuous operation at approximately 450° C. has been excellent, however, the device must be heated gently to avoid mechanical failure initiated by thermal shock.

Humidity dependant impedance characteristics of the sensor pellets were evaluated by applying a low frequency a.c. signal (10 Hz) and measuring the resulting response as function of moisture, while the sensor is maintained at 400°–450° C.

Figure 9:
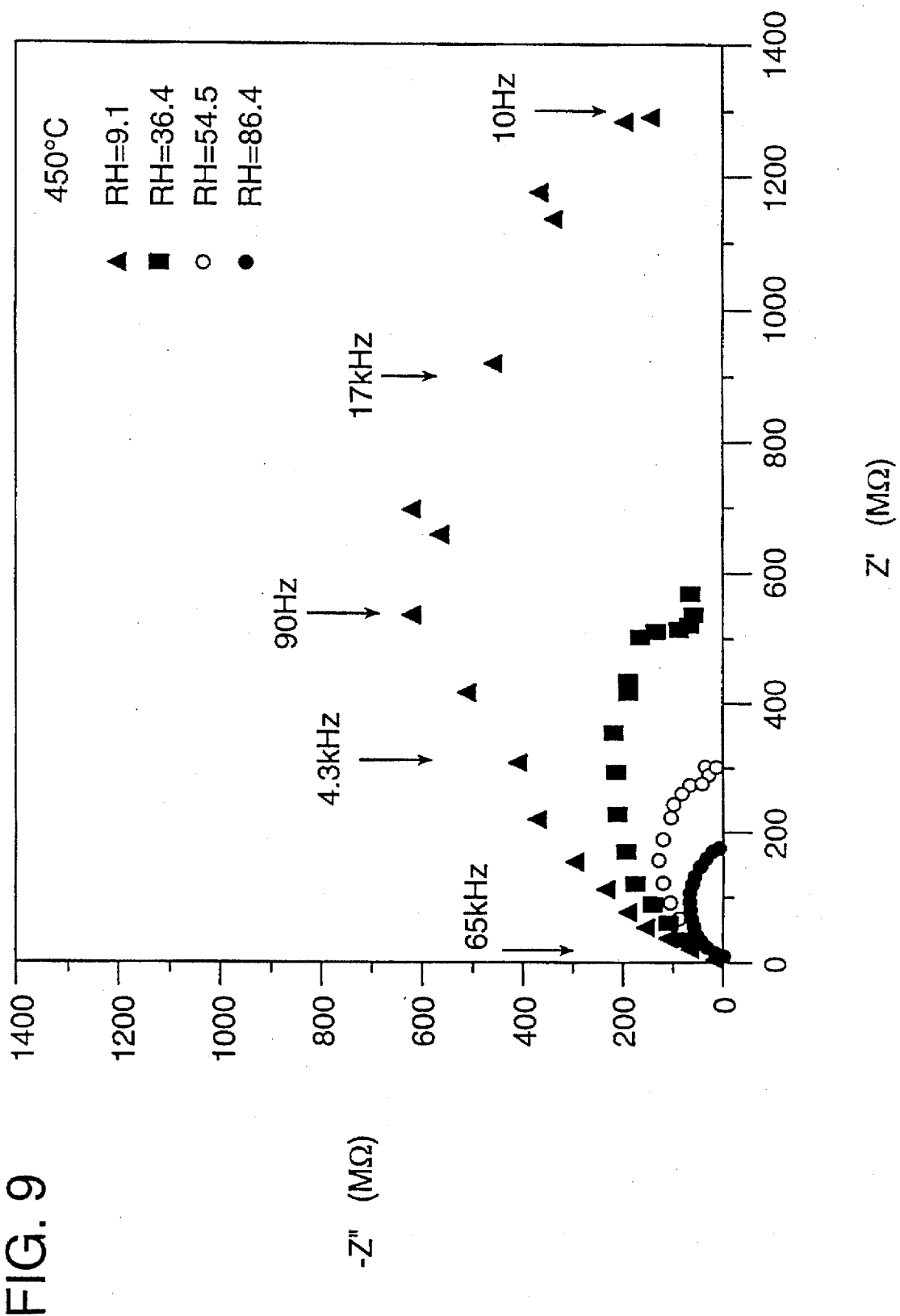
FIG. 9 is a graphical representation of the variation of the complex impedance of $HZr_2P_3O_{12}.ZrP_2O_7$ with charge of humidity at 450° C.

The impedance characteristics of the $HZr_2P_3O_{12}$-$ZRP_2O_7$ composite as a function of humidity have been evaluated earlier. FIG. 9 shows that the complex impedance of the composite at 450° C. decreases dramatically with increasing relative humidity.

Figure 10:
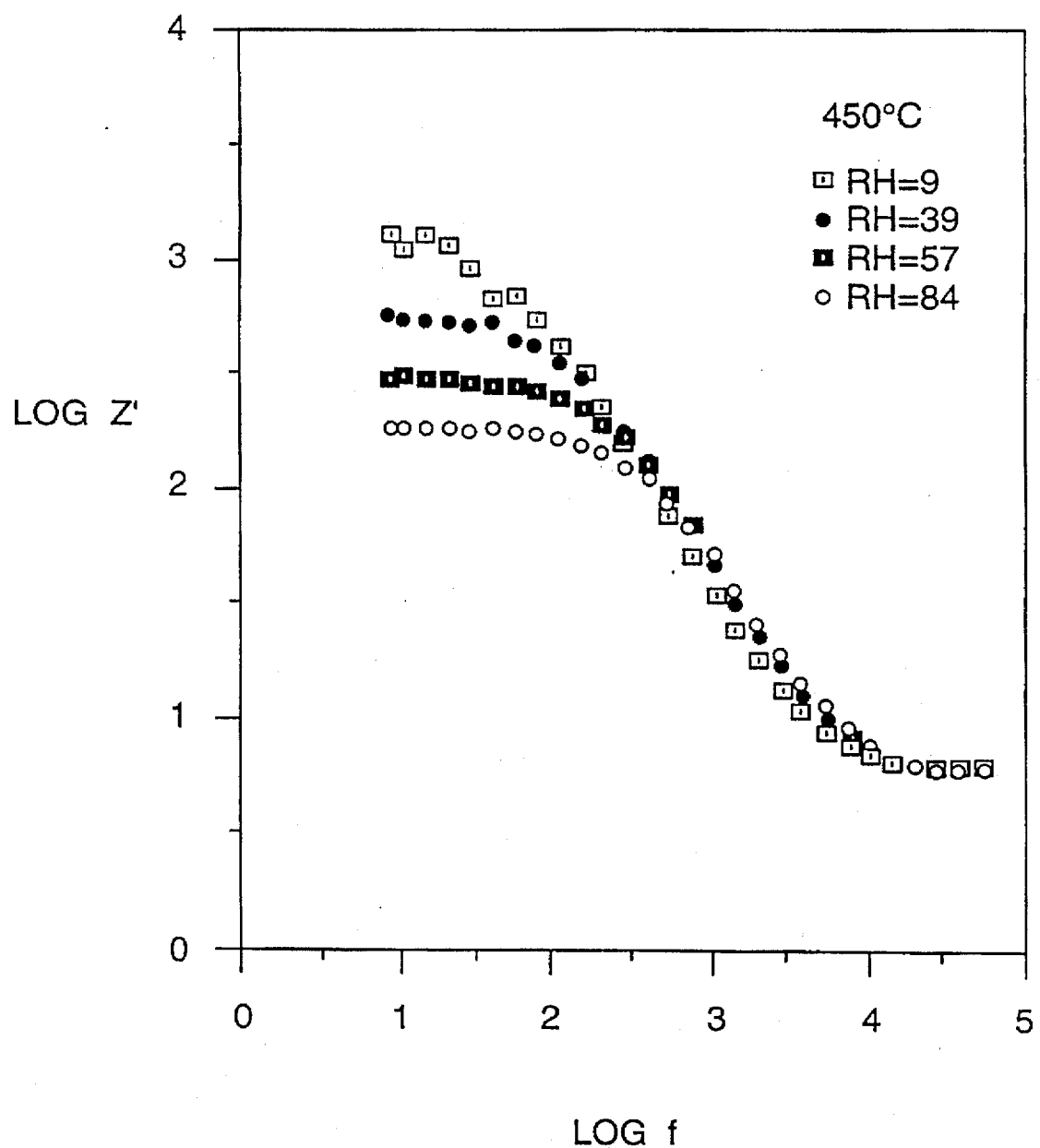
FIG. 10 is a graphical representation on coordinates impedance spectrum (log z') against relative humidity showing that conductivity is proportional to humidity.

It is evident from FIG. 10 that the real part of impedance as a function of humidity is frequency-independent in the low frequency region (10–20 Hz). This is advantageous for device application, because it requires the use of only a single low frequency for the measurement of impedance as a function of humidity. The a.c. conductivity (S), measured by impedance spectrum (log z'), is directly proportional to the humidity and is reproducible for each sample studied. The relationship between S and the relative humidity (RH) is:

$$s = A \cdot a^{(RH/100)}; \text{ where } A \text{ and } a \text{ are constants.} \quad \text{Eq.[5]}$$

Figure 11:
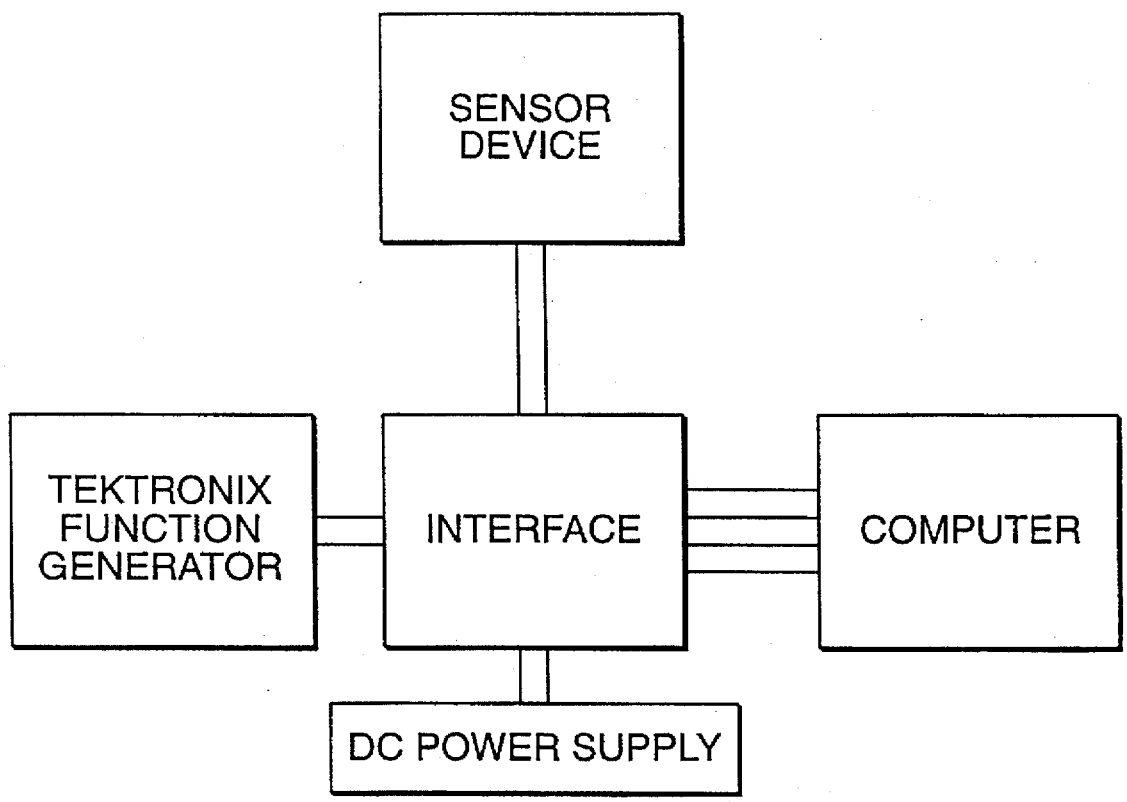
FIG. 11 is a schematic representation of the set up of the impedance type humidity sensor of the present invention.

The schematics of the measuring system are shown in FIG. 11. A Tektronix function generator may be used to apply a constant frequency of 12 Hz across the sensor. The signal is fed through a built-in Faraday box which is interfaced with a computer and the response in the form of phase shift can be recorded at different humidity and temperature conditions. Thus, the frequency generated by the generator is compared with frequency from the sensor. The measured impedance is related to the relative humidity according to Equation [5].

Figure 12A:
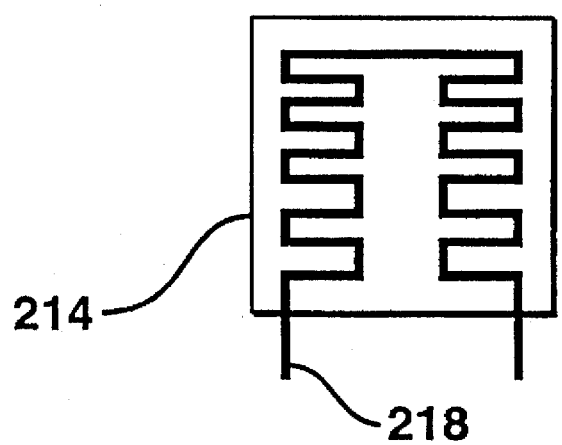
FIGS. 12a and 12b are schematic representations of another embodiment of an impedance cell type humidity sensor of the present invention employing film technology.
Figure 12B:
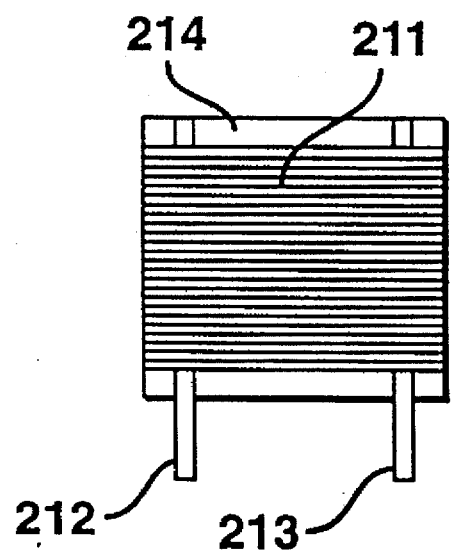

Another embodiment of $HZr_2(PO_4)_3 \cdot ZrP_2O_7$ composite as a humidity sensor is shown in FIG. 12. Again, the humidity sensor is based on a humidity sensitive material, for example $HZr_2(PO_4)_3 \cdot ZrP_2O_7$. The device is made by first screen printing two electrode contacts 212 and 213 on an alumina or other substrate 214 and then screen printing the humidity sensitive film 211 (e.g. $HZr_2(PO_4)_3$ or $HZr_2(PO4)_3 \cdot ZrP_2O_7$ composite) thereover (FIG. 12b). On the other side of the substrate 214 is the heater 218, which is made by printing thick film heater 218 of Pt or Ag or other desired material as shown in FIG. 12a. The heater is essentially a resistance wire attached to a power supply to provide current to heat the sensor to approximately 450° C. This type of construction permits the sensor to be constructed to a very small size (less than one square inch area).

Pastes of conducting metals, such as platinum and silver, or some ionic conductors are commercially available. There are three main components in these pastes: the active materials (metal, ceramic or ionic conductor), the fluxing agents (glass frit and bismuth oxide) and the organic solvents and binders. Composition can be varied to meet specific property requirements (viscosity, thermal expansion, grain size, surface properties).

A thin or thick humidity sensitive film comprising $HZr_2P_3O_{12}$ or $HZr_2P_3O_{12} \cdot ZrP_2O_7$ may be printed on the substrate over the electrode contacts. The film may be prepared from a sol-gel solution. The film may be printed, screen printed, spin-coated or applied onto the substrate in any manner known in the art. The film could range from a thickness of a few angstroms to many thousands of angstroms. Alternatively, the film could be prepared as a paste, in a similar manner to the preparation of the pellets hereinbefore discussed, and then painted onto the substrate.

The platinum electrodes are hooked up to the output, and the impedance is measured. The circuit is completed by the humidity sensitive film extending between the electrodes on the substrate. The impedance gives a direct relationship to humidity, which is read and interpreted by a computer. Like the previous embodiment, the sensor of this embodiment is interconnected with a computer and a function generator as shown in FIG. 11.

While the invention has been described in detail in the foregoing specification and the exemplary embodiments have been alluded to for purposes of illustration, it will be understood by those skilled in the art that such has been solely for purposes of exposition only and are not to be construed as limiting.

What is claimed is:

1. An impedance cell humidity sensor comprising:

a substrate;

heating means affixed to one side of the substrate;

a pair of spaced apart electrodes affixed to the other side of the substrate;

a film of humidity sensitive material comprising a composite of $HZr_2P_3O_{12}$ and $ZrP_2O_7$ applied over and interconnecting the electrodes; and a function generator for applying a low frequency across the sensor.

2. The sensor of claim 1 wherein the low frequency applied across the sensor is in the range of 10–20 Hz.

3. The sensor of claim 1 wherein the low frequency applied across the sensor is approximately 12 Hz.

4. The sensor of claim 3 wherein the sensor operates in the temperature range of 350° C. and 600° C.

5. The sensor of claim 3 wherein the sensor operates at approximately 450° C.

6. The sensor of claim 1 wherein the electrodes are applied to the substrate by screen printing the electrodes thereon.

7. The sensor of claim 6 wherein the film of humidity sensitive material is applied to the substrate and the electrodes by screen printing the film thereon.

8. The sensor of claim 7 wherein the heating means comprises a resistance wire attached to the substrate.

9. The sensor of claim 8 wherein the heating means is applied to the substrate by printing the resistance wire on the substrate.

* * * * *